United States Patent [19]

Copes et al.

[11] 3,988,318
[45] Oct. 26, 1976

[54] LOW MOLECULAR WEIGHT COMPLEXES OF LACTAMS AND POLYHYDROXY AROMATIC COMPOUNDS

[75] Inventors: Joseph P. Copes, Easton, Pa.; David I. Randall, Leland, Mich.

[73] Assignee: GAF Corporation, New York, N.Y.

[22] Filed: Oct. 10, 1974

[21] Appl. No.: 513,875

Related U.S. Application Data

[63] Continuation-in-part of Ser. No. 193,974, Oct. 29, 1971, abandoned.

[52] U.S. Cl. ............................. 260/239.3 R; 71/67; 71/88; 71/94; 71/95; 252/106; 252/107; 260/293.75; 260/293.77; 260/326.5 FL; 260/326.5 FN; 424/65; 424/244; 424/267; 424/274; 424/358

[51] Int. Cl.$^2$............... C07D 207/24; C07D 210/00; C07D 211/06

[58] Field of Search.......... 260/326.5 FN, 326.5 FL, 260/239.3 R, 293.75, 293.77

[56] References Cited
OTHER PUBLICATIONS

Schmulbach et al., *J. Org. Chem.*, 29:3122, (1964).

*Primary Examiner*—Frederick E. Waddell
*Attorney, Agent, or Firm*—Walter C. Kehm; Marilyn J. Maue

[57] ABSTRACT

A low molecular weight complex of a lactam and a hydroxy phenolic compound having the formula:

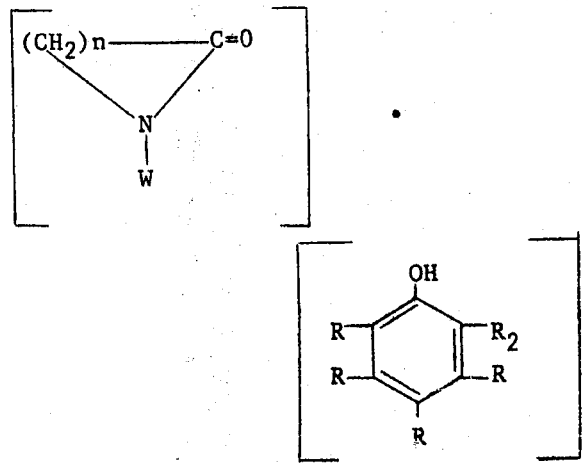

wherein $n$ is an integer of 3 to 5; W is hydrogen or alkyl having from 1 to 8 carbon atoms including cycloalkyl substituents; each R or $R_2$ is alkoxy of from 1 to 4 carbon atoms, hydrogen, halogen, hydroxyl, nitro, cyano, carboxylamino, alkylhydroxy having from 1 to 4 carbon atoms or alkyl having from 1 to 10 carbon atoms, and wherein $R_2$ can also be alaninyl or a hydroxy benzyl radical having the formula

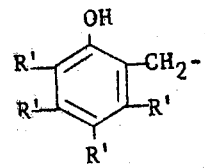

where R' is hydroxyl, cyano, alkyl having from 1 to 6 carbon atoms, hydrogen or halogen and wherein at least one R or $R_2$ is hydroxy when $R_2$ is other than a hydroxy benzyl radical.

12 Claims, No Drawings

LOW MOLECULAR WEIGHT COMPLEXES OF LACTAMS AND POLYHYDROXY AROMATIC COMPOUNDS

This application is a continuation-in-part of application Ser. No. 193,974, filed Oct. 29, 1971, now abandoned, all commonly disclosed subject matter of which is incorporated herein by reference.

The plurality of —OH groups in the phenolic moiety of the complex products of this invention is responsible for unexpected advantages in that the two or more hydroxy substituents provide greatly reduced hygroscopicity as compared with monohydroxybenzene. Thus, the products of the present invention are particularly adapted for incorporation in a solid vehicle or carrier in a form such as tablets, pellets, etc., which are resistant to deterioration or liquification under conditions of high humidity. Because of the low hygroscopicity of the polyhydroxy benzenes and corresponding complexes, the concentration depletion of the phenolic moiety is controlled at a more uniform rate and is not affected by weather conditions. Also, the present products are economically produced since they are readily crystallized from water.

The present complexes additionally possess unexpectedly strong reducing and antioxidizing properties so that they are excellent plasticizers in preventing oxidation of plastic films and fibers. Since the complex absorbs oxygen, it minimizes the tendency of oxygen to enter the polymeric structure and cause weakening of the plastic material.

Still another important advantage of the present complex compounds is their reduced toxicity. It is well known that phenol is toxic and is readily absorbed by the skin causing, in some cases, irritation and inflammation. However, polyhydroxy substituted benzenes are non-irritating to the skin and form complexes which are extremely stable even at elevated temperature. These complexes also display resistance to chemical deterioration by alkaline materials. As a result of these unusual properties, the present complexes are particularly useful in antiseptic soaps or liquids and as skin emollients where applied in creams, lotions, and mud packs, etc., since they effectively destroy bacteria without causing irritation to the skin.

The complexes of the invention are also useful as germicides, insecticides, wood preservatives, and agents permitting the controlled and gradual release of polyhydroxy phenolic compounds. The presence of two or more —OH groups, particularly —OH groups in the 1, 3 and/or 4 positions on the same phenyl ring or 1-, 1'-positions on vicinal phenyl rings is distinguished over phenol in improved stability.

The present invention relates to low molecular weight complexes of lactams and polyhydroxy aromatic compounds. More particularly, it is concerned with low molecular weight crystalline lactam-hydroxy phenolic complexes having a carbonyl infrared band at 1650 cm$^{-1}$ representing a shift of this band from 1680 cm$^{-1}$, which characterizes the carbonyl of the uncomplexed lactam.

It has been postulated that lactams and other amides form complexes with phenol; however, the prior art is totally lacking in any disclosure or teaching of definitely characterized chemical entities. Thus, for instance, Schmulbach et al. (J. Org. Chem. 29, 3122-4, 1964) has reported studies including thermodynamic data based on the addition of phenol to a series of amide solutions including solutions of N-methylvalerolactam, epsilon-caprolactam, N,N-dimethylacetamide, N,N-dimethylpropionamide, N,N-dimethylformamide, N-methylcaprolactam and N-methylpyrrolidone. The reactions were carried out in carbon tetrachloride; however, no actual compounds were isolated or characterized to establish that a complex, as opposed to a chemical mixture, was formed.

For the purposes of this disclosure, the hydroxyphenolic compounds or polyhydroxy aromatic compounds referred to herein, include phenols containing at least two —OH groups bonded to a single benzene ring and phenols containing one or more —OH groups bonded to a benzene ring which in turn is bonded to a benzyl ring containing one or more —OH groups.

In accordance with the present invention, well defined, low molecular weight crystalline complexes of lactams and hydroxy phenolic compounds have now been prepared.

The compounds of the present invention can be represented by the structural formula

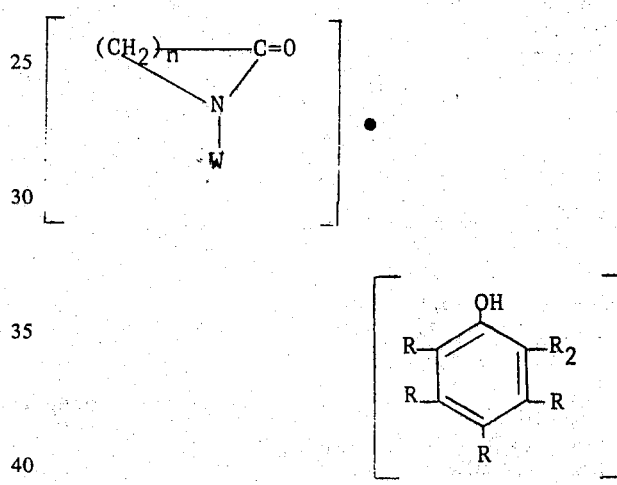

wherein $n$ is an integer of 3 to 5; W is hydrogen, alkyl having from 1 to 8 carbon atoms including cycloalkyl substituents, the alkyl group preferably having 1 to 6 carbon atoms; each R or $R_2$ is alkoxy having from 1 to 4 carbon atoms, hydrogen, cyano, nitro, amido, halogen, hydroxyl, or alkyl having from 1 to 10 carbon atoms preferably having from 1 to 4 carbon atoms, alkylhydroxy having from 1 to 4 carbon atoms and wherein $R_2$ can also be alaninyl or a hydroxy benzyl radical having the formula

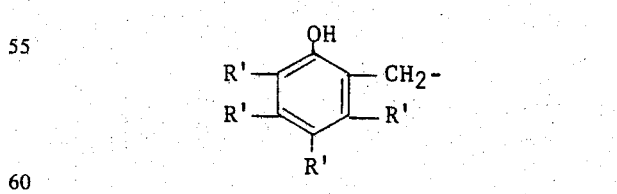

where each R' is hydroxyl, hydrogen, cyano, or alkyl having from 1 to 6 carbon atoms, preferably a hydroxy benzyl or mono-substituted hydroxy benzyl group and wherein at least one R or $R_2$ is hydroxy when $R_2$ is other than a hydroxybenzyl, Most preferred of the above complex compounds are those wherein the hydroxy phenolic compound is hydroquinone or a hydroxy, cyano, chloro or alkyl substituted hyroquinone or unsubstituted or chlorinated hydroxybenzylphenol.

The compounds of the foregoing structural formulae can be generally prepared by admixing the lactam and the hydroxy phenolic compound and isolating the well defined crystalline complex thereby formed. The complex compounds of this invention are formed in a 2:1 ratio of the hydroxyl groups to lactam group eg. pyrrolidone or caprolactam.

The difunctional hydroxy phenol, as in hydroquinone, functions as two independent phenolic hydroxyls in most cases. Thus, one mol of pyrrolidone reacts with one hydroquinone molecule. Also in the case of N-methyl-2-pyrrolidone, one molecule of the latter reacts with one molecule of hydroquinone to form the corresponding complex.

The lactams of the present invention can be prepared by one of several known methods including the reaction of a lactone (eg. 4-hydroxy butyric acid lactam) with ammonia or an alkyl amine wherein the alkyl group is as defined for W in the above formula. The reaction to form the lactam is generally carried out at a temperature between about 150° and about 325° C. Also, the hydroxy phenolic compounds employed in this invention can be prepared methods known in the art, for example, by alkaline fusion of phenol sulfonic acids or polychlorobenzenes. In general, halogens are substituted on the phenol ring by reaction with hydrogen halide or halogen; and cyano groups are substituted by reaction of the hydroxy phenol with cyanic acid or cuprous cyanide. Numerous additional methods for preparing the compounds which form the present phenolic moieties are set forth in the art; however, the preparation of these phenolic compounds is not intended to form part of the invention as defined in the appended claims.

In carrying out the complexing reaction of this invention, it is usually advantageous to agitate or agitate and heat the mixture of hydroxyphenolic compound and lactam in the presence of absence of a solvent until a clear, homogeneous liquid is obtained, although applied heating may not be necessary in every case in view of the exothermic nature of the complexing reaction. More specifically, the complexing reaction can be carried out at a temperature between about room temperature and up to about the boiling point of the complex; although a temperature in excess of 180° C. is usually not required. However, in order to obtain a slower rate of reaction, temperatures as low as about −10° C. can be employed, if desired. The preferred temperature at which the reactants are mixed is within the range of from about room temperature and about 150° C. For the present reaction, there is no preferred order of addition of the reactants to the reaction zone; however, it has been found beneficial to agitate the mixture during the complexing reaction. Usually, the reaction takes place in a relatively short period of time, i.e., from a few seconds to a few minutes, most often immediately upon contact after liquification of the reactive species. However, the contacting of reactants can be continued for a period of several hours (eg. 2 hours) to insure completion of reaction. While it is preferred to conduct the reaction under atmospheric pressure, slightly subatmospheric or, in the case of relatively low boiling materials, slightly elevated pressures, from about 10mm Hg to about 25 psig, are also contemplated.

The lactam and phenolic compound are contacted in a mol ratio generally between about 10:1 and about 1:10, preferably between about 5:1 and 1:3.

It is important that the mol ratio be maintained within the broad range since, with higher concentration of lactam, an intractable solution is formed in which product crystallization does not take place and recovery of the product from the thickened solution is practically impossible. Conversely, the phenolic compound when employed in excess of 10:1 also causes difficulty in product recovery since separation of the normally solid polyhydroxy compound from the normally solid complex is extremely difficult. In view of these considerations, it is most preferred to maintain a mol ratio as close to 1:2 lactam to polyhydroxy reactant as convenient and practical.

The lactam and hydroxyphenolic reactants of the present invention can be contacted in the presence or absence of a solvent. When both reactants are used in the form of solid particles, they can be mixed and heated to form a melt in the reaction zone. In cases where one of the reactants is a liquid, eg., the lactam species, the liquid reactant can be heated to a temperature above the melting point of the solid reactant and the solid mixed and added thereto. Still another method of contacting the reactive species includes mixing a solution of either one or both of the reactants. Specifically, the components of the reaction can be admixed by first forming a separate solution of each and gradually adding the solutions to the reactor or the components in the same solvent may be separately added to the reactor. Still another method comprises adding the components to a common liquid medium contained in a reactor. The concentration of each component in the solvent or dispersant is between about 1% by weight and up to the saturation limit of the liquid at the temperature employed. The more concentrated solutions are preferred. Suitable solvents for the lactam and polyhydroxy species include water, chloroform, carbon tetrachloride, benzene, toluene, hexane, heptane, acetic acid, cyclohexane, xylene and isooctane, mixtures thereof or any of those indicated in the following Examples. If desired, a stabilizing agent may be added to the reaction mixture in a concentration of from 0.5% to 8% or higher. Suitable stabilizing agents are well known in the art and include hydrocarbon esters and 2,6-substituted hydrocarbon phenols.

After the complex is formed, which is usually marked by an exotherm or an exothermic rise in the temperature, the reactor is cooled, by allowing to cool gradually, by rapid cooling or by flash chilling, generally to a temperature between about 40° and about 5° below the reaction temperature or that at which the crystalline product is formed. The solvent is then removed by decantation and/or evaporation and the product is washed at a temperature between about 0° and about 60° C with a suitable liquid such as hot water, or any of the above named solvents for the reactive species, and the wash liquid removed. The product is then recrystallized by warming with solvent until dissolved and then chilling. This procedure can be repeated as often as necessary to achieve the desired purity of the complex product. In some cases, when crystals are not formed with normal cooling, it may be desirable to cool the product liquid mixture to significantly lower temperatures, eg., down to about −40° C., in order to initiate a crystalline state.

In regard to the reaction and subsequent separation and washing procedure, it is to be considered most surprising that the complexes are stable to hot solvents and in particular to hot water. In fact, complexes formed in accordance with the invention could be crystallized out of water without decomposition.

Examples of suitable hydroxyphenols for use in accordance with the invention include: hydroxyphenol, diredmanol, hydroxycresol, orcinol, hydroquinone, 3,4-dichloro-2-hydroxyphenol, hexachlorophene, hexabromophene, 3,5,6-trichloro-2-hydroxyphenol, 4-amido-3-hydroxyphenol, or, m-, p-bromohydroxyphenol chlorohydroxyphenol or fluorohydroxyphenol, catechol, 4-chloro-2,5-dimethyl-3-hydroxyphenol, phloroglucinol, 2-ethyl-4-hydroxyphenol, 2,6-dimethoxyhydroxyphenol 4-ethyl-3-hydroxyphenol, resacetophenone, 4-methylcatechol, 1,3,4,1',3',4',-hexachlorodiredmanol, 2-nonyl hydroxyphenol, 2-propyl-4,5-dihydroxyphenol, resorcinol, 4-cyanohydroxyphenol, 2-nitroresorcinol, 4-decyl-3-hydroxyphenol, pyrogallol, and those mentioned in the appended Examples.

Examples of suitable lactams include N-cyclohexyl-2-pyrrolidone, N-octyl-2-pyrrolidone, 2-pyrrolidone, e-caprolactam, N-methyl-2-pyrrolidone, N-propyl-2-pyrrolidone, N-heptyl-2-pyrrolidone, α-piperidone, N-methyl piperidone, N-cyclobutyl-2-pyrrolidone, β-propriolactam, and the like, together with those mentioned in the appended Examples.

The compounds in accordance with the invention have proved to be suitable as detoxified germicides. Phenols, although excellent germicides in themselves, are frequently irritating to the skin. The detoxification takes place in part due to the improved stability of the lactam-hydroxyphenolic complex which results in restricted release of the hydroxyphenolic moiety and the reduced toxicity of the phenol containing a plurality of —OH groups. For these reasons, the present complexes have been found to be suitable for use as deodorants, antiseptic soaps, etc. It has also been found advantageous to use the complexes in accordance with the invention to avoid the result where such concentrations of chlorinated phenols are used that bodies of water are polluted thereby. Thus, the complexes of the hydroxyphenols and the lactams of the invention can be used to detoxify such phenols and are superior and important purification agents for drinking water from lakes and rivers.

The complexes are also suitable in dye applications acting as dye carriers for polyester fibers, etc., and have been found to be particularly useful as antioxidants. The complexes result in reduced vapor pressure of the phenol involved, thus resulting in greater persistence in applications and less odor and drifting of the medicament in connection with which they are used. Thus, the present complexes are useful as sterilants, insecticides, larvicides, arachnidicides, nematocides, herbicides and the like, providing for release of the phenolic moiety over greater periods and for prolonged substantially uniform effect with respect to retarded leaching of the active agent in the environment in which they are used.

More specific illustrations of the usefulness of the compounds of the invention are the incorporation thereof into calamine lotion, hexachlorophene, isopropanol, witch hazel, neutral oils or into face creams, vanishing cream, medicating creams, vaseline or bees wax bases as superior anti-itching agents, as an antioxidant in slushing oils, hydraulic fluids and lube oils, as protective thermoplastic coatings for metals, as an active agent in germicidal compositions, an anti-rancidity agents for edible fats, as antigas fading agents for dyed cellulose acetate fibers and films, as stabilizing agents for monomers, rubber antioxidants, and the like.

The complex compounds of this invention can be employed in the above applications by dispersing the complex in a suitable inert solvent or carrier such as talc, diatomaceous earth, calamine lotions, soaps, creams, whale oil, dibutyl phthalate, cetyl palmitate, dimethyl phthalate, neutral oils, hexachlorophene, isopropanol, acetone, methylethyl ketone, water, glycerin, petroleum or mineral oil, butanol, propanol, 100 SUS pale oil, Igepal, beeswax base, benzene, toluene, xylene, cyclohexane or any of the solvents mentioned above or in the following Examples or mixtures thereof and are employed therein concentrations between about 0.001 and about 25% by weight depending upon the particular application and the effective amount desired. In this regard skin emollients will preferably contain between 0.05% and 5% by weight; algacides between 0.001 and 1% by weight; herbicides, sterilants, insecticides, etc. between 0.5 and 20% by weight; antioxidants between 0.01 and 5% by weight and plasticizers and stabilizers between 2% and 10% by weight. Generally the present complex compounds are incorporated with a carrier or in a standard formulation by admixing therewith, preferably at a temperature from about room temperature to about 130° C until a uniform mixture is obtained.

This invention will appear more fully from the examples which follow. These examples are set forth by way of illustration only, and it will be understood that the invention cannot be construed as limited in spirit or in scope by the details contained therein and that other species listed above can be substituted in the examples which follow to provide the corresponding lactam-polyhydroxyphenol complexes which are useful in the above applications. Although the complexes of the following examples are generally useful in the applications recited above; in each instance a particular use is indicated by way of illustration which specific use is not to be construed as limiting to the general fields of application for the particular complex set forth. All values in the following examples are by weight unless otherwise indicated.

EXAMPLE 1

PREPARATION OF N-METHYL-2-PYRROLIDONE COMPLEX WITH HYDROQUINONE (1:1)

In a reaction zone, 11.1 g (0.10 mol) hydroquinone and 9.94 g. (0.10 mol) N-methyl-2-pyrrolidone are heated to 135° C with constant agitation to form the complex thereof and the resulting liquid complex is crystallized at 98° C. The entire crystalline mass which is formed is dissolved in 35cc toluene at 110° C., allowed to cool to room temperature, filtered free of toluene and dried in a vacuum oven at 40° C. The N-methyl-2-pyrrolidone hydroquinone complex has a melting point of 85°–98° C.

The same quantities of said reactants plus 10cc of water yield a crystalline precipitate which is identical to the toluene crystallized material. In this case the crystalline complex has a melting point of 96°–98.52° C.

Analysis for the complex prepared by precipitation from water.

| | Calculated | % Found |
|---|---|---|
| C | 63.2 | 63.1 |
| N | 6.7 | 6.4 |
| H | 7.2 | 7.2 |

The above results establish that new compound contains 1 molecule of the dihydroxy compound complexed with 1 molecule of N-methyl-2-pyrrolidone, this being consistent with the aforementioned ratio of 2 phenolic hydroxyls per pyrrolidone ring.

In the infrared spectrum, a new band appeared at 6.2 microns, the 7.14 micron band in N-methyl-2-pyrrolidone has shifted to 7.20 microns, the 5.92 carbonyl band shifted from 5.92 microns to 6.00 microns, the hydroquinone band at 12.0 microns shifted to 11.95 microns and a new band appeared at 12.5 microns.

This complex is particularly useful as an antioxidant for fats in a concentration preferably between about 0.01 and about 0.5% by weight. This complex is also useful in removing skin blemishes such as freckles, liver spots, and darkened areas when compounded by admixing in a vanishing cream base at a concentration of between 2% and 5% by weight. Other uses for this complex include a fungicide against phytophthora infestations when incorporated with a carrier by admixing in a concentration between about 0.5% and about 5% by weight.

EXAMPLE 2

It was attempted to complex vinyl pyrrolidone and hydroquinone; however, only an admixture was obtained and the formation of any complex was not detected inasmuch as only the starting materials could be isolated in the product mixture.

EXAMPLE 3

In an attempt to complex dimethyl formamide and hydroquinone, 14.6 g. (0.2 mol) dimethyl formamide and 22.0 g. (0.2 mol) hydroquinone were admixed and the mixture warmed until homogeneous. No crystals were initially formed, however, on standing for 2 days at room temperature, some crystals separated out. These were isolated and identified as being hydroquinone and not the complexed compound.

EXAMPLE 4

PEPARATION OF N-METHYL-2-PYRROLIDONE COMPLEX WITH 2,4,5-TRICHLORO-RESORCINOL (1:1)

At about 40° C in a reaction zone, 0.10 mol (21.3 g.) 2,4,5-trichloro-resorcinol and 0.10 mol (9.9 g.) N-methyl-2-pyrrolidone are slurried together, whereupon the temperature rises about 30°. A clear homogeneous liquid is produced by further heating to 90° C., which liquid partially solidifies on being cooled 30° C. Crystallization out of n-heptane yields the crystalline complex of N-methyl-2-pyrrolidone.2,4,5-trichloro resorcinol. This complex is particularly useful as a slimicide preferably employed in a concentration between about 0.05% and bout 1.5% by weight with respect to a carrier such as water, or other inert carriers for example, for use on papermill brake beaters.

EXAMPLE 5

PREPARATION OF N-CYCLOHEXYL-2-PYRROLIDONE-HYDROQUINONE COMPLEX (1:1)

In a reactor 0.10 mol hydroquinone (11.0 g.) and 0.10 mol (16.7 g.) N-cyclohexyl-2-pyrrolidone are stirred together at room temperature. An intimate mixture is formed and a 6° C. rise in temperature occurs. The resulting slurry is heated to 80° C whereupon a clear liquid is formed. On cooling in an ice bath, the solution slowly crystallizes to form a magma of the complex compound. The crystals melt at 52°–57° C. This complex is particularly useful as an antioxidant preferably employed in a concentration between about 0.1% and about 5% by weight when employed in a system such as a silverplating bath. This complex is also contemplated for use as an anti-rancidity agent for use with fats and can be suitably incorporated in soaps.

EXAMPLE 6

PREPARATION OF PYRROLIDONE COMPLEX WITH 3-ETHOXY-PYROCATECHOL (1:1)

In a reactor 0.20 mol (17.0 g.) 2-pyrrolidone and 0.20 mol (15.4 g.) 3-ethoxy-pyrocatechol are warmed together to a temperature of 60° C. Prior to such heating, there is an increase in the temperature of the mixture indicating the formation of the complex. The complex compound thereafter recovered; namely, the 1:1 complex of pyrrolidone-3-ethoxy pyrocatechol, is a low melting, crystalline, solid which is highly soluble in toluene and water.

This complex is particularly useful as an antioxidant preferably employed in a concentration of from about 0.1% to about 5% by weight when used with a suitable carrier such as natural, neutral, or drying oils.

EXAMPLE 7

PREPARATION OF CAPROLACTAM COMPLEX WITH HYDROQUINONE (1:1)

In a reactor 0.20 mol caprolactam (22.6 g.) and 0.10 mol hydroquinone (11.1 g.) are warmed at 130° C. until a homogeneous liquid is obtained. The solid complex is crystallized out of toluene and melted at 117°–119° C. When the solid complex is crystallized out of water, the melting point is exactly the same.

Elemental analysis for $C_{12}H_{17}NO_3$ gave the following values:

| | % Calculated | % Found | (Toluene) |
|---|---|---|---|
| C | 64.5 | 64.1 | |
| H | 7.64 | 8.59 | |
| N | 6.28 | 7.95 | |

This example illustrates that although the caprolactam and the hydroquinone is added in a mol ratio of 2:1, the resulting complex is formed in a 1:1 mol ratio, i.e., one lactam to one hydroquinone is obtained. Accordingly, it is established that one lactam group reacts with two hydroxy groups in the present reactions. This complex is particularly useful as a high speed developer for photographic negatives in a concentration of from about 4% to about 10% by weight with respect to a carrier such as water or other inert material.

EXAMPLE 8

PREPARATION OF PYRROLIDONE COMPLEX WITH 2,4,5-TRICHLORO-RESORCINOL (1:1)

A mixture of 0.10 mol 2-pyrrolidone (1.5 g.) and 0.10 mol (22 g.) 2,4,5-trichloro-resorcinol are heated together at 80° C. On cooling, a crystalline solid is formed which is crystallized from n-heptane and yields the complex 2-pyrrolidone.2,4,5-trichlororesorcinol product which is a water insoluble crystalline complex and identifiable by the shift of the carbonyl band from 1680cm$^{-1}$ to 1650cm$^{-1}$.

This complex is particularly useful as an algacide in a concentration of from about 0.001 to about 0.1% by weight, e.g., with respect to water as in a swimming pool.

EXAMPLE 9

PREPARATION OF CAPROLACTAM COMPLEX WITH 3-BUTYL-PYROCATECHOL (1:1)

In a reactor 0.20 mol caprolactam (22.6 g.) is mixed together and warmed at 70° C. until a homogeneous liquid is formed. On chilling of the liquid, a solid forms and 40cc of n-heptane is added to the mixture and stirred with warming to form a saturated solution. Crystallization from n-heptane yields the caprolactam. 3-butyl-pyrocatechol complex in a pure state. This complex is particularly useful as a plasticizer in concentrations between about 2% and about 10% by weight with respect to a carrier, such as for example, polystyrene or any other suitable polymer.

EXAMPLE 10

PREPARATION OF N-METHYL-2-PYRROLIDONE COMPLEX WITH 4-NITRO-RESORCINOL (1:1)

A mixture of 0.2 mol (31.0 g.) 4-nitro-resorcinol and 0.20 mol (10 g.) N-methyl-2-pyrrolidone is heated to 120° C. Prior to initiating the heating, a slight exotherm is noted indicating the complex has formed. On cooling, a solid is obtained which is the above N-methyl-2-pyrrolidone.4-nitro-resorcinol. This complex may be used for example as slimicide as described in Example 4.

EXAMPLE 11

PREPARATION OF N-PROPYL PYRROLIDONE COMPLEX WITH 2,2'-METHYLENE BIS (2,4-DICHLOROPHENOL) (1:1)

A slurry is prepared from 8.2 g. (0.025 mol) 2,2'-methylene bis (4,6-dichlorophenol), and 3.2 g. (0.025 mol) of N-propyl pyrrolidone and intimately mixed. An exotherm of 10° C. is evidence that the complex is formed. The slurry is melted at a temperature of 130° C. and then stirred for 10 minutes. On cooling, a crystalline solid is obtained. Crystallization out of heptanetoluene yields the N-propyl pyrrolidone 2,2'-methylene bis (2,4-dichorophenol) complex.

Although this complex possesses substantially good activity in the applications mentioned above, it is particularly useful as a bacteriostat employed in concentrations preferably between about 1% and about 3% by weight with respect to a carrier such as soap or liquid cleansing medium. This complex is also useful when added to drinking water in the above concentrations for the control of worms (eg. ringworm, tapeworm) in cattle, poultry, dogs, cats, and other animals.

EXAMPLE 12

PREPARATION OF N METHYL-2-PYRROLIDONE HEXACHLOROPHENE COMPLEX (1:1)

A slurry is prepared from 10.2 grams (0.25 mol) of hexachlorophene and 24.8 grams (0.25 mol) of N-methyl-2-pyrrolidone and intimately mixed in a glass reactor. An exotherm of 8° C. is evidenced and a solid product is formed which is the N-methyl-2-pyrrolidone hexachlorophene complex. The slurry is melted at about 120° C. and then stirred for 15 minutes. On cooling, a crystalline solid is obtained. The crystals are dissolved in hexane-toluene (50/50) solvent and separated by decantation and evaporation.

The complex of this example possesses high germicidal activity against *Salmonella aureus* as well as *Pseudomonas aeroginosa* and *Bacillus subtilis*, and other bacteria that are commonly found on the skin and may be employed in a concentration of 2% to 5% by weight in a suitable carrier such as soap cake or liquid and applied as a lather to the skin to prevent acne or other skin eruptions or rashes. This complex is also particularly useful as a skin emollient and antiseptic in the above concentrations and may be incorporated in applications for the skin such as mud packs, lotions and neutralizers.

EXAMPLE 13

PREPARATION OF PYRROLIDONE.HEXACHLOROPHENE COMPLEX (1:1)

A slurry is prepared from 101.7 grams (0.25 mol) of hexachlorophene and 21.3 grams (0.25 mol) of pyrrolidone and intimately mixed in a glass reactor. An exotherm of 8° C. is evidenced and a solid product is formed which is the pyrrolidonehexachlorophene complex. The slurry is melted at about 120° C. and then stirred for 15 minutes. On cooling, a crystalline solid is obtained. The crystals are dissolved in hexane-toluene (50/50) solvent and after cooling are recrystallized and separated by decantation and evaporation.

The complex of this example possesses high germicidal activity against *Salmonella aureus* as well as

[ N-Propyl 2-Pyrrolidone] • 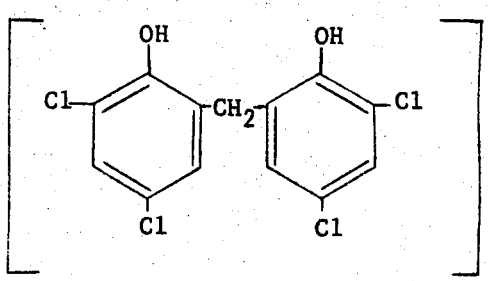

*Psuedomonas aeroginosa* and *Bacillus subtilis*, and may be employed in a concentration of 0.5% to 5% by weight in a suitable carrier such as tincture of green soap for hospital use as a preoperative scrubbing agent.

This complex is also particularly useful as a skin emollient and may be formulated in a concentration between about 0.5% and 3% by weight by admixing in conventional skin preparations which include any of those mentioned above.

EXAMPLE 14

PREPARATION OF 2-PYRROLIDONE COMPLEXED WITH HYDROQUINONE (1:1)

A mixture of 8.5 g. 2-pyrrolidone and 10.5 g. hydroquinone are heated and stirred until a homogeneous liquid phase is obtained. The melt is maintained at about 100° C for 30 minutes whereupon it is chilled to about 20° C. A crystalline solid is formed, melted and recrystallized from toluene to provide the 2-pyrrolidone.hydroquinone complex. This complex, like that of Example 7, is particularly useful as a high speed developer for photographic negatives.

It is to be understood that any of the specific lactams or phenols previously mentioned can be substituted in any of the above examples to provide equally useful complex compounds.

What is claimed is:

1. A low molecular weight crystalline lactam.hydroxyphenol complex having the formula:

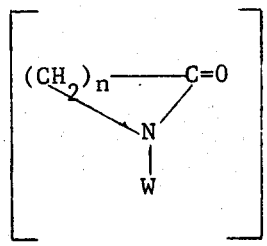

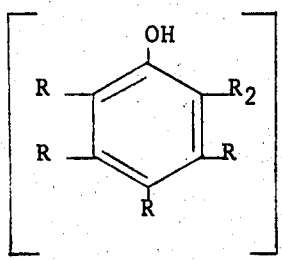

wherein $n$ is an integer of 3 to 5; W is hydrogen or alkyl having from 1 to 8 carbon atoms, including cycloalkyl substituents; each R and $R_2$ is alkoxy of from 1 to 4 carbon atoms, amido, alkylhydroxy of from 1 to 4 carbon atoms, cyano, nitro, hydrogen, halogen, hydroxy or alkyl of from 1 to 10 carbon atoms and wherein $R_2$ can also be alaninyl or a hydroxybenzyl radical having the formula:

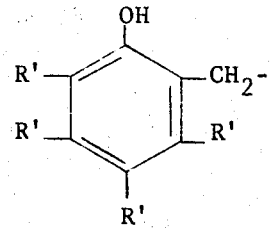

where R' is hydrogen, hydroxyl, cyano, halogen or alkyl of from 1 to 6 carbon atoms, and wherein at least one R is hydroxyl when $R_2$ is other than a hydroxyl or a hydroxybenzyl radical.

2. The crystalline lactam.hydroxyphenol complex of claim 1 wherein W is hydrogen or alkyl having from 1 to 6 carbon atoms; each R and $R_2$ is hydrogen, hydroxy, chlorine, methyl, or ethyl, and $R_2$ can also be alaninyl, hydroxybenzyl or a monosubstituted hydroxybenzyl radical and at least one R is hydroxy when $R_2$ is other than a hydroxy or a hydroxybenzyl radical.

3. A 1:1 complex according to claim 1 designated N-methyl-2-pyrrolidone.hydroxyphenol.

4. A 1.1 complex according to claim 1 designated N-methyl-2-pyrrolidone.2,4,5-trichloro resorcinol.

5. A 1:1 complex according to claim 1 designated N-methyl-2-pyrrolidone.3-ethyl hydroquinone.

6. A 1:1 complex according to claim 1 designated N-cyclohexyl-2-pyrrolidone.hydroquinone.

7. A 1:1 complex according to claim 1 designated pyrrolidone. 3-ethoxypyrocatechol.

8. A 1:1 complex according to claim 1 designated N-propylpyrrolidone.2,2'-methylene bis(2,4-dichlorophenol).

9. A 1:1 complex according to claim 1 designated caprolactam.hydroquinone.

10. A 1:1 complex according to claim 1 designated N-methyl-2-pyrrolidone.hexachlorophene.

11. A 1:1 complex according to claim 1 designated pyrrolidone.hexachlorophene.

12. A 1:1 complex according to claim 1 designated N-methyl-2-pyrrolidone.hydroquinone.

* * * * *